United States Patent [19]

Müller et al.

[11] Patent Number: 4,758,670
[45] Date of Patent: Jul. 19, 1988

[54] MICROBICIDAL AND GROWTH-REGULATING COMPOSITIONS

[75] Inventors: Urs Müller, Münchenstein; Hermann Rempfler, Ettingen; Hans Tobler, Allschwil, all of Switzerland

[73] Assignee: Ciba-Geigy Corporation, Ardsley, N.Y.

[21] Appl. No.: 567,998

[22] Filed: Jan. 4, 1984

[30] Foreign Application Priority Data

Jan. 10, 1983 [CH] Switzerland ............ 112/83

[51] Int. Cl.$^4$ ............ C07D 249/08; A01N 43/64
[52] U.S. Cl. ............ 548/262; 548/101; 548/341; 71/92; 71/76
[58] Field of Search ............ 548/101, 262, 341; 424/245, 269, 273 R; 71/76, 92; 514/184, 383, 399

[56] References Cited

U.S. PATENT DOCUMENTS 4,359,470 11/1982 Kramer et al. ............ 548/262
4,382,944  5/1983 Kramer et al. ............ 548/262
4,428,949  1/1984 Kramer et al. ............ 548/262

FOREIGN PATENT DOCUMENTS 0061835 10/1982 European Pat. Off. ............ 548/262

OTHER PUBLICATIONS

Burger, Medicinal Chemistry, (Second Edition, New York, 1960), p. 1055.

*Primary Examiner*—Glennon H. Hollrah
*Assistant Examiner*—D. Dinner
*Attorney, Agent, or Firm*—Edward McC. Roberts; Meredith C. Findlay

[57] ABSTRACT

Fluoroazolylpropane derivatives of the formula I

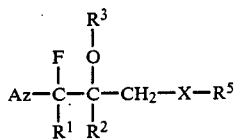

are described, in which Az is imidazolyl or triazolyl, $R^1$ is hydrogen, alkyl or aralkyl which is unsubstituted or substituted by halogen, alkyl, alkoxy, halogenoalkyl, nitro, cyano, carboxyl or alkoxycarbonyl, $R^2$ is $C_1$–$C_{10}$-alkyl which is unsubstituted or substituted by alkoxy, aralkoxy or phenyl, it being possible for the aromatic nuclei of aralkoxy and phenyl in turn to be unsubstituted or substituted by halogen, alkyl, alkoxy, halogenoalkyl, cyano, carboxyl or alkoxycarbonyl, $R^3$ is hydrogen, alkyl, alkylcarbonyl or aralkyl which is unsubstituted or substituted by halogen, alkoxy, alkyl, halogenoalkyl, cyano, carboxyl or alkoxycarbonyl, $R^5$ is an unsubstituted or monosubstituted or polysubstituted radical selected from the series comprising $C_1$–$C_8$-alkyl, $C_3$–$C_8$-cycloalkyl, $C_3$–$C_6$-alkenyl, $C_3$–$C_6$-alkynyl, phenyl, naphthyl, biphenyl, benzylphenyl, benzyloxyphenyl, phenoxyphenyl and aralkyl, and X is oxygen or sulfur; including the acid addition salts, quaternary azolium salts and metal complexes.

Methods of preparing these products are also disclosed, as are agrochemical compositions containing one of these compounds as the active substance. A process for controlling phytopathogenic microorganisms and/or for regulating plant growth by means of these substances is also described.

2 Claims, No Drawings

MICROBICIDAL AND GROWTH-REGULATING COMPOSITIONS

The present invention relates to novel, substituted fluoroazolylpropane derivatives and to acid addition salts, quaternary azolium salts and metal complexes thereof. The invention also relates to the preparation of these substances and to microbicidal and growth-regulating compositions containing at least one of these compounds as the active substance. The invention also relates to the preparation of the said compositions and to the use of the active substances or the compositions for regulating plant growth and for controlling harmful microorganisms. The invention also relates to fluoroazolylmethyloxiranes and fluoroazolyl ketones which have been prepared as intermediates.

The fluoroazolylpropane derivatives according to the invention have the formula I

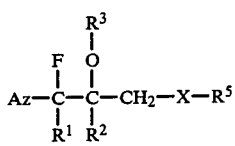

in which Az is imidazolyl or triazolyl, $R^1$ is hydrogen, alkyl or aralkyl which is unsubstituted or substituted by halogen, alkyl, alkoxy, halogenoalkyl, nitro, cyano, carboxyl or alkoxycarbonyl, $R^2$ is $C_1-C_{10}$-alkyl which is unsubstituted or substituted by alkoxy, aralkoxy or phenyl, it being possible for the aromatic nuclei of aralkoxy and phenyl in turn to be unsubstituted or substituted by halogen, alkyl, alkoxy, halogenoalkyl, cyano, carboxyl or alkoxycarbonyl, $R^3$ is hydrogen, alkyl, alkylcarbonyl or aralkyl which is unsubstituted or substituted by halogen, alkoxy, alkyl, halogenoalkyl, cyano, carboxyl or alkoxycarbonyl, $R^5$ is an unsubstituted or monosubstituted or polysubstituted radical selected from the series comprising $C_1-C_8$-alkyl, $C_3-C_8$-cycloalkyl, $C_3-C_6$-alkenyl, $C_3-C_6$-alkynyl, phenyl, naphthyl, biphenyl, benzylphenyl, benzyloxyphenyl, phenoxyphenyl and aralkyl, and X is oxygen or sulfur; including the acid addition salts, quaternary azolium salts and metal complexes.

The term azolyl characterises a five-membered heterocyclic five-ring containing nitrogen as the hetero-atom and having aromatic character. Typical representatives are 1H-1,2,4-triazole, 4H-1,2,4-triazole and 1H-imidazole. The term alkyl itself or as a constituent of another substituent, such as alkoxy, alkylthio, halogenoalkyl, aralkyl or alkylcarbonyl, is to be understood, depending on the number of carbon atoms indicated, as meaning, for example, the following groups: methyl, ethyl, propyl, butyl, pentyl, hexyl, heptyl, octyl, nonyl or decyl and isomers thereof, for example isopropyl, isobutyl, sec.-butyl, tert.-butyl, isopentyl etc. Halogenoalkyl is a monohalogenated to perhalogenated alkyl substituent, for example $CHCl_2$, $CHF_2$, $CH_2Cl$, $CCl_3$, $CH_2F$, $-CH_2CH_2Cl$, $CHBr_2$ etc. Here and in the following text, halogen is to be understood as meaning fluorine, chlorine, bromine or iodine, preferably fluorine, chlorine or bromine and especially fluorine and chlorine. Naphthyl is α-naphthyl or β-naphthyl, preferably α-naphthyl. Alkenyl is, for example, 1-propenyl, allyl, 1-butenyl, 2-butenyl or 3-butenyl, and alkynyl is, for example, 1-propynyl or propargyl. Aryl is, for example, naphthyl, particularly phenyl, and aralkyl is a lower alkyl radical which is substituted by an aromatic group, for example benzyl or phenylethyl. Depending on the number of carbon atoms, cycloalkyl is, for example, cyclopropyl, cyclobutyl, cyclopentyl, cyclohexyl, cycloheptyl, cyclooctyl etc.

The present invention relates both to the free organic molecules of the formula I and to acid addition salts, quaternary azolium salts and metal complexes thereof. The free molecules are preferred. Examples of salt-forming acids are inorganic acids: a hydrogen halide acid, such as hydrofluoric acid, hydrochloric acid, hydrobromic acid or hydriodic acid, and sulfuric acid, phosphoric acid, phosphorous acid and nitric acid, and organic acids, such as acetic acid, trifluoroacetic acid, trichloroacetic acid, propionic acid, glycollic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, trifluoromethanesulfonic acid, salicylic acid, p-aminosalicylic acid, 2-phenoxybenzoic acid or 2-acetoxybenzoic acid.

Metal complexes of the formula I consist of the parent organic molecule and an inorganic or organic metal salt, for example the halides, nitrates, sulfates, phosphates, acetates, trifluoroacetates, trichloroacetates, propionates, tartrates, sulfonates, salicylates, benzoates etc., of the elements of the third and fourth main groups, such as aluminium, tin or lead, and of the first to eighth subgroups, such as chromium, manganese, iron, cobalt, nickel, copper, zinc, silver, mercury etc. The subgroup elements of the 4th period are preferred. The metals can be present in these complexes in the various valencies appropriate to them. The metal complexes of the formula I can exist in a mononuclear or polynuclear form, i.e. they can contain one or more organic molecular moieties as ligands. Complexes containing the metals copper, zinc, manganese and tin are preferred.

1-Hydroxyethylazole derivatives are known as plant growth-regulators and fungicides from the literature, for example from European Patent Application No. 40,345.

The compounds, according to the invention, of the formula I are oils, resins or, mainly, solids which are stable at room temperature and which are distinguished by very valuable microbicidal and growth-regulating properties. They can be employed in a preventive or curative manner in the agricultural sector or related fields, for controlling microorganisms which damage plants and for regulating plant growth, the triazolylmethyl derivatives within the scope of the formula I being preferred. The active substances, according to the invention, of the formula I are distinguished by being very well tolerated by crop plants.

Compounds which are preferred by virtue of their pronounced growth-regulating and/or microbicidal action are those in which Az is imidazolyl or 1,2,4-triazolyl, $R^1$ is hydrogen, $C_1-C_6$-alkyl which is unsubstituted or substituted by halogen or cyano, or $C_1-C_3$-phenylalkyl which is unsubstituted or substituted by halogen, $C_1-C_3$-alkyl, $C_1-C_3$-alkoxy, $C_1-C_3$-halogenoalkyl, nitro, cyano, carboxyl or $C_1-C_6$-alkoxycarbonyl, $R^2$ is $C_1-C_{10}$-alkyl which is unsubstituted or substituted by $C_1-C_3$-alkoxy, phenyl or $C_1-C_3$-phenylalkyl, it being possible for the phenyl nuclei in turn to be unsubstituted or substituted by halogen, $C_1-C_3$-alkyl, $C_1-C_3$-alkoxy, $C_1-C_3$-halogenoalkyl, nitro, cyano, carboxyl or $C_1-C_6$-alkoxycarbonyl, $R^3$ is hydrogen, $C_1-C_6$-alkyl, $C_1-C_6$- alkylcarbonyl or $C_1$-$C_3$-phenylalkyl which is unsubstituted or substituted by halogen, $C_1$-$C_3$-alkoxy, $C_1$-$C_3$-alkyl, $C_1$-$C_3$-halogenoalkyl, cyano, carboxyl or $C_1$-$C_6$-alkoxycarbonyl, $R^5$ is an unsubstituted or monosubstituted or polysubstituted radical selected from the series comprising $C_1$-$C_8$-alkyl, $C_3$-$C_8$-cycloalkyl, $C_3$-$C_6$-alkenyl, $C_3$-$C_6$-alkynyl, phenyl, naphthyl, biphenyl, benzylphenyl, benzyloxyphenyl, phenoxyphenyl and aralkyl, the substituents being selected from the series comprising halogen, cyano, $C_1$-$C_3$-alkyl, $C_1$-$C_5$-alkoxy, $C_1$-$C_5$-halogenoalkyl, $C_1$-$C_3$-alkylthio, $C_1$-$C_3$-halogenoalkyl, $C_1$-$C_3$-halogenoalkylthio, nitro and/or thiocyano, and X is oxygen or sulfur.

Subgroups which may be mentioned as enjoying a further preference are those comprising compounds of the formula I in which (a) Az is 1,2,4-triazolyl or (b) $R^2$ is $C_1$-$C_6$-alkyl or benzyl which is unsubstituted or substituted by halogen or (c) $R^1$ and $R^3$ are hydrogen or $C_1$-$C_4$-alkyl or (d) $R^5$ is phenyl which is substituted by halogen or (e) X is oxygen.

Within the subgroup (b), preferred compounds are those in which $R^2$ is tert.-butyl or i-propyl.

Within subgroup (d), preferred compounds are those in which $R^5$ is phenyl which is substituted in the 4-position by halogen.

Compounds which should be mentioned as a particularly preferred subgroup of compounds of the formula I are those in which Az is 1,2,4-triazolyl, $R_1$ and $R_3$ are hydrogen or $C_1$-$C_4$-alkyl, $R_2$ is tert.-butyl or i-propyl, $R_5$ is phenyl which is substituted in the 4-position by halogen and X is oxygen.

The following are examples of preferred individual compounds: 1-(4-fluorophenoxy)-2-tert.-butyl-2-hydroxy-3-fluoro-3-(1H-1,2,4-triazol-1-yl)-propane, 1-(4-fluorophenoxy)-2-tert.-butyl-2-hydroxy-3-fluoro-3-methyl-3-(1H-1,2,4-triazol-1-yl)-propane, 1-(4-chlorophenoxy)-2-tert.-butyl-2-hydroxy-3-fluoro-3-(1H-1,2,4-triazol-1-yl)-propane, 1-(4-chlorophenoxy)-2-tert.-butyl-2-hydroxy-3-fluoro-3-methyl-3-(1H-1,2,4-triazol-1-yl)-propane and 1-(4-methylphenoxy)-2-tert.-butyl-2-hydroxy-3-fluoro-3-methyl-3-(1H-1,2,4-triazol-1-yl)-propane.

The compounds of the formula I are prepared by processes known per se.

Thus the compounds of the formula I are obtained by reacting an azolylmethyloxirane of the formula II

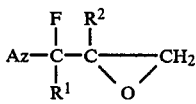 (II)

in which $R^1$, $R^2$ and Az are as defined under formula I, in the presence of a base and in an inert solvent, with an alcohol or thioalcohol of the formula III $$H-X-R^5 \qquad (III)$$

in which X and $R^5$ are as defined under formula I, and, if desired, by etherifying or esterifying the resulting product of the formula Ia

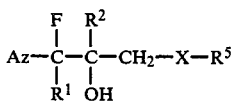 (Ia)

by reacting it with an etherifying or esterifying agent of the formula IV $$Y-R^3 \qquad (IV)$$

in which $R^3$ is as defined under formula I and Y is a halogen atom or an organic or inorganic acid radical.

The reactions (II with III) is advantageously carried out in the presence of catalytic amounts of bases as condensation agents. Suitable condensation agents are organic and inorganic bases, for example tertiary amines, such as trialkylamines (trimethylamine, triethylamine, tripropylamine etc.), pyridine and pyridine bases (4-dimethylaminopyridine, 4-pyrrolidylaminopyridine etc.), oxides, hydrides and hydroxides, carbonates and bicarbonates of alkali and alkaline earth metals (CaO, BaO, NaOH, LiOH, $CaH_2$, KOH, NaH, $Ca(OH)_2$, $KHCO_3$, $NaHCO_3$, $Ca(HCO_3)_2$, $K_2CO_3$ and $Na_2CO_3$), and alkali metal acetates, such as $CH_3COONa$ or $CH_3COOK$. In addition, alkali metal alcoholates, such as $C_2H_5ONa$, $n-C_3H_7ONa$, $(CH_3)_3CO-K$ etc., are also suitable.

The reaction (II with III) is preferably carried out in an organic solvent which is relatively polar, but inert towards the reaction, for example N,N-dimethylformamide, N,N-dimethylacetamide, dimethyl sulfoxide, acetonitrile, benzonitrile, ethylene glycol dimethyl ether, diethylene glycol dimethyl ehter, triethylene glycol dimethyl ether, dioxane, tetrahydrofuran and others. Reactions of this type can, however, also be carried out in combination with other solvents which are inert towards the reaction, for example benzene, toluene, xylene, hexane, petroleum ether, chlorobenzene, nitrobenzene and others. The reaction temperatures are within a temperature range from 20° C. to 250° C., preferably 80° C. to 180° C.

The optional conversion of the compounds of the subformula Ia into the compounds of the formula I in which $R^3$ has a definition other than hydrogen is advantageously carried out in an inert organic solvent. Suitable solvents are aprotic solvents, such as N,N-dimethylformamide, N,N-dimethylacetamide, dimethyl sulfoxide, acetonitrile, benzonitrile, N-methylpyrrolidone, N-methylpiperidone, benzene, toluene, xylene, hexane, cyclohexane, chlorobenzene, nitrobenzene and others.

In the event that the $-O-R^3$ group is an ether group, Y is usually halogen, such as chlorine, bromine and iodine, or acid radicals derived from strong acids, such as sulfuric acid, phosphoric acid, sulfonic acids, preferably halogenoalkylsulfonic acids, or halogenoalkanecarboxylic acids, such as trifluoroacetic acid. Typical representatives of such acid derivatives are dimethyl sulfate, diethyl sulfate and methyl trifluoromethanesulfonate. In the event that the $-O-R^3$ group is an ester group, Y is generally halogen, such as chlorine or bromine, or acid radicals of acids which can form an anhydride with the acyl radical which is transferred. This is preferably an anhydride containing the same acid. Consequently, the reagent $Y-R^3$ is then, for example, acetic anhydride, propionic anhydride, benzoic anhydride, benzenesulfonic anhydride or trifluoromethanesulfonic anhydride.

The etherification or esterification of the compounds of the subformula Ia is advantageously effected in the presence of bases, such as alcoholates, hydroxides, hydrides, carbonates or bicarbonates of alkali or alkaline earth metals. The reaction temperatures are 20°-150° C., preferably 60°-120° C.

The compounds of the formula I are obtained in the form of mixtures of diastereomers. The invention relates to all the diastereomeric forms of the active substances of the formula I and to mixtures thereof. It therefore embraces both the pure diastereomers and the individual optical isomers of the enantiomer pairs which are embraced.

The alcohols or thioalcohols of the formula III and also the etherifying and esterifying agents of the formula IV are known or are prepared by methods known per se.

The oxiranes of the formula II are novel; they are intermediates which have been specially developed for the preparation of the valuable active substances of the formula I. Because of their structure, they can be converted in a simple manner into the compounds of the formula I. The compounds of the formula II thus represent a further aspect of the present invention.

The oxiranes of the formula II can be prepared by reacting the parent ketones of the formula V

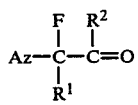

(V)

in which $R^1$, $R^2$ and Az are as defined under formula I, in the presence of strong bases, such as alkali and alkaline earth metal alcoholates, alkali metal hydroxides or alkali or alkaline earth metal hydrides, in dimethyl sulfoxide or one of the other solvents described for the reaction of II with III, with dimethylsulfonium methylide, dimethyloxosulfonium methylide or the corresponding salts, such as trimethylsulfonium iodide or trimethyloxosulfonium iodide. Under suitable circumstances, it is also possible to effect the production of the sulfonium ylide or the reaction of the sulfonium salt with the base by the phase transfer process. The following could be used as suitable phase transfer catalysts: quaternary ammonium salts, such as trialkylphenylalkylammonium salts or tetraalkylammonium salts, quaternary phosphonium salts, such as tetraalkylphosphonium salts, or crown ethers, such as 15-crown-5 or 18-crown-6. In this reaction, the sulfonium ylide is formed in situ and reacts directly with the ketone of the formula V to give the oxirane of the formula II. The reaction is carried out at temperatures from 0° to 120° C.

Analogous reactions are known from the literature; cf. JACS, 87, 1353 (1965). In principle, the reaction can be carried out analogously to the reactions described therein.

Ketones of the formula V can be prepared from the α-halogenoketones, which are known per se, of the formula VI

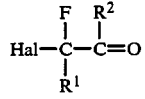

(VI)

in which $R^1$ and $R^2$ are as defined under formula I and Hal is chlorine or bromine, by reacting these compounds, in the presence of a base, with azoles of the formula VII

 (VII)

in which Az is as defined under formula I.

The ketones of the formula V can also be obtained by reacting an azolylmethyl ketone of the formula VIII

 (VIII)

in the presence of a base with a compound of the formula IX

 (IX)

in which $R^1$ is as defined under formula I and Z is a halogen atom or an organic or inorganic acid radical.

The preparation of the ketones of the formula V is effected in the conventional inert solvents and, if desired, at an elevated temperature.

The compounds of the formulae VI, VII, VIII and IX are known and are in some cases commercially available or can be prepared by known methods.

The intermediates of the formula V, which have been developed specially for the synthesis of the compounds of the formula I, form a further subject of the present invention.

In principle, unless expressly specified in an individual case, one or more solvents or diluents, inert to the reaction, can be present when any of the starting materials, intermediates and end products mentioned herein are prepared. Suitable examples are aliphatic and aromatic hydrocarbons, such as benzene, toluene, xylenes or petroleum ether; halogenated hydrocarbons, such as chlorobenzene, methylene chloride, ethylene chloride, chloroform, carbon tetrachloride or tetrachloroethylene; ethers and ether-like compounds, such as dialkyl ethers (diethyl ether, diisopropyl ether, tert.-butyl methyl ether etc.), anisole, dioxane or tetrahydrofuran; nitriles, such as acetonitrile or propionitrile; N,N-dialkylated amides, such as dimethylformamide; dimethyl sulfoxide; ketones, such as acetone, diethyl ketone or methyl ethyl ketone, and mixtures of such solvents with one another. In some cases it can also be advantageous if the reaction is, or partial stages of a reaction are, carried out under an atmosphere of a protective gas and/or absolute solvents. Suitable protective gases are inert gases, such as nitrogen, helium or argon, or in certain cases also carbon dioxide.

The process of preparation described, including all its partial stages, is an important part of the present invention.

It has now been found, surprisingly, that the new active substances of the formula I or compositions containing these active substances are especially distinguished by the fact that they intervene in a controlled manner in the metabolism of plants. This controlled intervention in the physiological processes of plant development makes it possible to use the active substances of the formula I for various purposes, in particular for purposes associated with increasing the yield of useful plants, facilitating harvesting and saving labour in the course of measures taken for crops of plants.

According to experience hitherto, it is a fact relevant to the mode of action of plant growth regulators that an active substance can exert one or more different effects on plants. The effects of the substances depend essentially on the time of the application, relative to the stage of development of the seed or of the plant, and on the quantities of active substances applied to the plants or their habitat, and on the mode of application. In every case growth regulators are intended to have a favourable effect on the crop plants in the manner desired.

Plant growth-regulating substances can be employed, for example, for inhibiting vegetative plant growth. Inhibition of growth in this way is of economic interest, inter alia, in the case of grasses, since it makes it possible, for example, to reduce the frequency of cutting the grass in ornamental gardens, parks and sports grounds or on road verges. Another important aspect is inhibition of the growth of herbaceous and woody plants on road verges and in the neighbourhood of overhead transmission lines or very generally in areas in which considerable ground vegetation is undesirable.

The use of growth regulators for inhibiting the growth in height of cereals is also important, since the risk of the plants bending over ("lodging") before the harvest is reduced or completely eliminated by shortening the stems. In addition, growth regulators can cause a strengthening of the stems of cereals, which also counteracts lodging.

In the case of many crop plants, inhibition of vegetative growth permits the crop to be cultivated more densely, so that an increased yield based on the area of soil can be achieved.

A further mechanism for increasing yields by means of growth inhibitors depends on the fact that the nutrients benefit the formation of flowers and fruit to a greater extent, while vegetative growth is restricted.

Growth regulators frequently also make it possible to achieve promotion of vegetative growth. This is of great benefit when the vegetative parts of the plants are harvested. Promoting vegetative growth can, however, also result at the same time in promotion of generative growth so that, for example, more fruit or larger fruit is formed.

In some cases increases in yield can also be achieved by intervention in the plant metabolism, for example by increasing the efficiency of photosynthesis, without changes in vegetative growth manifesting themselves. Growth regulators can also cause a change in the composition of plants, so as to produce a better quality of harvested products. Thus it is possible, for example, to increase the content of sugar in sugar beet, sugar cane, pineapples and citrus fruits or to raise the protein content in soya or cereals.

The development of parthenocarpic fruit can also take place under the influence of growth regulators. It is also possible to affect the sex of the flowers.

Growth regulators also make it possible to exert a favourable influence on the production or outflow of secondary plant substances. Stimulating the flow of latex in rubber trees may be mentioned as an example.

Lateral branching can also be increased by breaking the apical dominance by chemical means as the result of using growth regulators during plant growth. This is of interest, for example, in the propagation of plants by cuttings. However, it is also possible to inhibit the growth of side shoots, for example in order to prevent the formation of side shoots in tobacco plants after the latter have been decapitated, and thus to promote leaf growth.

The premature falling of fruit can be prevented by using growth regulators. However, it is also possible to promote the fall of fruit to a certain extent—for example in the case of table fruit—in the sense of thinning out by chemical means. Growth regulators can also be used to reduce the force required to detach the fruit of crop plants at the time of harvesting, so as to enable the plants to be harvested mechanically or to facilitate manual harvesting.

Growth regulators also make it possible to accelerate or to retard ripening of the harvested crop before or after harvesting. This is particularly advantageous, because it makes it possible to produce optimum adjustment to the demands of the market. Furthermore, growth regulators can improve the colouration of fruit in some cases. In addition, it is also possible to concentrate ripening to a particular point in time by means of growth regulators. This provides the conditions necessary to enable complete mechanical or manual harvesting of, for example, tobacco, tomatoes or coffee, to be carried out in only a single process.

The use of growth regulators also makes it possible to affect the dormant period of seeding or budding in plants, i.e. the endogenous annual rhythm, so that the plants, for example pineapples or ornamental plants in nurseries, germinate, sprout or flower at a time at which they normally show no readiness to do so.

Growth regulators also make it possible to retard the sprouting of buds or the germination of seeds, for example in order to avoid damage caused by late frosts in regions subject to frost. On the other hand, it is possible to stimulate the growth of roots and/or the formation of shoots, so that growth can be limited to a shorter period of time.

Growth regulators can also render crop plants halophilic. This provides the conditions necessary to enable the cultivation of plants to be carried out on soils containing salt.

Resistance to frost and drought can also be induced in plants by means of growth regulators.

The aging (senescence) of plants or parts of plants can be inhibited or retarded under the influence of growth regulators. An effect of this type can be of great economic interest, because it is possible to improve or prolong the capacity of treated parts of plants or whole plants, such as fruit, berries, vegetables, lettuce or ornamental plants, to be stored after harvesting. It is also possible to achieve a considerable increase in yield via prolonging the phase of photosynthetic activity by treating crop plants.

A further important field of application for growth inhibitors is their use for inhibiting excessive growth in tropical soil-covering plants, cover crops as they are called. In tropical and subtropical monocultures, for example in palm plantations, cotton fields, maize fields etc., soil-covering plants, especially species of leguminosae, are frequently planted alongside the actual crop plants and serve to maintain or improve the quality of the soil (prevention of desiccation and provision of nitrogen) and to prevent erosion (denudation by wind and water). By applying the active substances according to the invention, it is now possible to control the growth of these cover crops and thus to keep the height to which these soil-covering plants grow at a low level, so as to ensure that the crop plants grow in a healthy manner and the soil is maintained in a favourable condition.

It has also been found, surprisingly, that the active substances of the formula I or corresponding compositions not only have advantageous growth-regulating properties, but also have a microbicidal spectrum which is very advantageous for practical requirements. A further field of use of compounds of the formula I is, therefore, the control of harmful microorganisms, especially phytopathogenic fungi. Thus the compounds of the formula I possess a curative, preventive and systemic action for the protection of plants, in particular crop plants, which is very advantageous for practical requirements, without affecting these plants adversely.

The active substances of the formula I make it possible to inhibit or destroy the microorganisms which occur on plants or parts of plants (fruit, flowers, foliage, stalks, tubers or roots) of various useful crops, and parts of the plants which grow later also remain protected from microorganisms of this type.

The active substances are effective against phytopathgenic fungi belonging to the following classes: Ascomycetes (for example Venturia, Podosphaera, Erysiphe, Monilinia and Uncinula); Basidiomycetes (for example the genera Hemileia, Rhizoctonia and Puccinia); and *Fungi imperfecti* (for example Botrytis, Helminthosporium, Fusarium, Septoria, Cercospora and Alternaria). In addition, the compounds of the formula I have a systemic action. They can also be employed as dressing agents for treating seed (fruit, tubers or grain) and plant cuttings to protect them against fungal infections and can also be employed against phytopathogenic fungi which occur in the soil. The active substances according to the invention are distinguished by being particularly well tolerated by plants.

The invention also relates, therefore, to microbicidal compositions and to the use of the compounds of the formula I for controlling phytopathogenic microorganisms, in particular fungi which damage plants, and to the prophylactic prevention of attack on plants.

In addition, the present invention also includes the preparation of agrochemical compositions, which comprises mixing the active substance intimately with one or more substances or groups of substances described herein. It also includes a process for treating plants which is distinguished by the application of the compounds of the formula I and/or of the novel compositions.

Within the scope of this invention, the following species of plants rank as examples of target crops for the fields of indication disclosed herein: cereals: (wheat, barley, rye, oats, rice, sorghum and related crops); beet: (sugar beet and fodder beet); pome, stone and soft fruit: (apples, pears, plums, peaches, almonds, cherries, strawberries, raspberries and blackberries); leguminous plants: beans, lentils, peas and soya); oil crops: (rape, mustard, poppy, olives, sunflowers, coconuts, castor oil plants, cocoa and ground nuts); cucurbitaceae: (pumpkins, cucumbers and melons); fibre plants: (cotton, flax, hemp and jute); citrus fruit: (oranges, lemons, grapefruit and mandarins); varieties of vegetables: (spinach, lettuce, asparagus, cabbage species, carrots, onions, tomatoes, potatoes and capsicum); lauraceae: (avocado, cinnamon and camphor); or plants such as maize, tobacco, nuts, coffee, sugar cane, tea, grapes, hops and banana and natural rubber plants. Within the scope of the present invention, however, plants are also any species of other green flora, either ornamental plants (composites), grasslands, embankments or general low cover crops which counteract erosion or desiccation of the soil, or cover crops such as are desirable in plantations of trees and shrubs (fruit plantations, hop fields, maize fields, vineyards etc.).

Active substances of the formula I are customarily used in the form of compositions and can be applied to the area or plant to be treated together with further active substances, simultaneously or successively.

These further active substances can be either fertilisers, trace element donors or other preparations which affect plant growth. They can, however, also be selective herbicides, insecticides, fungicides, bactericides, nematocides, molluscicides or mixtures of several of these preparations, together with, if appropriate, further carriers, surfactants or other application-promoting additives which are conventionally used in the art of formulation.

Suitable carriers and additives can be solid or liquid and correspond to the substances which are serviceable in the art of formulation, for example natural or regenerated mineral substances, solvents, dispersing agents, wetting agents, tackifiers, thickeners, binders or fertilisers.

A preferred process for applying an active substance of the formula I or an agrochemical composition containing at least one of these active substances is application to the foliage (leaf application). In this case the number of applications depends on the intensity of attack by the corresponding pathogen (variety of fungus) or the mode of influencing growth. The active substances of the formula I can, however, also reach the plants via the soil through the roots (systemic action), by the habitat of the plants being impregnated with a liquid preparation or the substances being introduced into the soil in a solid form, for example in the form of granules (soil application). The compounds of the formula I can, however, also be applied to seed grains (coating), either by impregnating the grains with a liquid preparation of the active compound or by coating them with a solid preparation. In addition, further modes of application are possible in special cases, for example controlled treatment of the plant stalks or the buds.

The compounds of the formula I are employed in an unaltered form or, preferably, together with the adjuncts which are conventional in the art of formulation, and are, therefore, processed in a known manner to give, for example, emulsion concentrates, brushable pastes, solutions which can be atomised or diluted without further treatment, dilute emulsions, wettable powders, soluble powders, dusts, granules and encapsulations in, for example, polymeric substances. The application processes, such as atomising, nebulising, dusting, sprinkling, brushing or watering, are selected to suit the intended aims and the given circumstances, as is also the type of composition. Advantageous application rates are, in general, 10 g to 5 kg of active substance (AS) per hectare; preferably 100 g to 2 kg of AS per hectare and particularly 200 g to 600 g of AS per hectare.

The formulations, that is to say the compositions, preparations or combinations containing the active substance of the formula I and, if appropriate, a solid or liquid adjuvant, are prepared in a known manner, for example by intimately mixing and/or grinding the active substances with diluents, for example solvents, solid carriers and, if appropriate, surface-active compounds (surfactants).

The following can be suitable as solvents: aromatic hydrocarbons, preferably the fractions from $C_8$ to $C_{12}$, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol or ethylene glycol monomethyl or monoethyl ether, ketones, such as cyclohexanone, strongly polar solvents, such as N- methyl-2-pyrrolidone, dimethyl sulfoxide or dimethylformamide, and vegetable oil which can be epoxidised, such as epoxidised coconut oil or soya oil; or water.

The solid carriers used, for example for dusts and dispersible powders, are, as a rule, natural ground minerals, such as calcite, talc, kaolin, montmorillonite or attapulgite. It is also possible to add highly disperse silica or highly disperse absorbent polymers in order to improve the physical properties. Suitable particulate, adsorptive granular carriers are porous types, for example pumice stone, broken brick, sepiolite or bentonite, while examples of suitable non-sorptive carriers are calcite or sand. In addition, it is possible to use a large number of pregranulated materials of an inorganic or organic nature, such as, in particular, dolomite or comminuted plant residues.

Depending on the nature of the active substance of the formula I to be formulated, suitable surface-active compounds are nonionic, cationic and/or anionic surfactants having good emulsifying, dispersing and wetting properties. Surfactants are also to be understood as meaning mixtures of surfactants.

Suitable anionic surfactants can be so-called water-soluble soaps as well as water-soluble synthetic surface-active compounds.

Suitable soaps are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids, which can be obtained, for example, from coconut oil or tallow oil. Furthermore, mention should also be made of the salts of fatty acid methyl taurides.

More frequently, however, so-called synthetic surfactants are used, in particular fatty sulfonates, fatty sulfates, sulfonated benzimidazole derivatives or alkylarylsulfonates.

The fatty sulfonates or sulfates are, as a rule, in the form of alkali metal salts, alkaline earth metal salts or substituted or unsubstituted ammonium salts, and contain an alkyl radical having 8 to 22 C atoms, in which connection alkyl also includes the alkyl moiety of acyl radicals, for example the Na or Ca salt of ligninsulfonic acid, of dodecylsulfuric acid ester or of a mixture of fatty alcohol sulfates prepared from natural fatty acids. These products also include the salts of the sulfuric acid esters and sulfonic acids of fatty alcohol/ethylene oxide adducts. The sulfonated benzimidazole derivatives preferably contain 2 sulfonic acid groups and a fatty acid radical having 8–22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product.

Furthermore, corresponding phosphates, for example salts of the phosphoric acid ester of a p-nonylphenol/-(4–14)-ethylene oxide adduct, and phospholipids are also suitable.

Suitable nonionic surfactants are primarily polyglycol ether derivatives of aliphatic or cycloaliphatic alcohols, saturated or unsaturated fatty acids and alkylphenols, and these derivatives can contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble adducts, containing 20 to 250 ethylene glycol ether groups and 10 to 100 propylene glycol ether groups, of polyethylene oxide with polypropylene glycol, ethylenediaminopolypropylene glycol and an alkylpolypropylene glycol having 1 to 10 carbon atoms in the alkyl chain. The said compounds usually contain 1 to 5 ethylene glycol units per unit of propylene glycol.

Examples of nonionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Furthermore, fatty acid esters of polyoxyethylenesorbitan, such as polyoxyethylenesorbitan trioleate, are also suitable.

The cationic surfactants are, in particular, quaternary ammonium salts which contain, as N-substituents, at least one alkyl radical having 8 to 22 C atoms and, as further substituents, lower alkyl radicals which can be halogenated, benzyl radicals or lower hydroxyalkyl radicals. The salts are preferably in the form of halides, methylsulfates or ethylsulfates, for example stearyltrimethylammonium chloride or benzyl-di-(2-chloroethyl)-ethylammonium bromide.

The surfactants which are customary in the art of formulation are described, inter alia, in the following publications: "McCutcheon's Detergents and Emulsifiers Annual", MC Publishing Corp., Ridgewood, N.J., 1981; H. Stache, "Tensid-Taschenbuch" ("Surfactants Handbook"), 2nd edition, C. Hanser Verlag, Munich, Vienna, 1981; M. and J. Ash, "Encyclopedia of Surfactants", vol. I–III, Chemical Publishing Co., New York, 1980–1981.

The pesticidal preparations contain, as a rule, 0.1 to 99%, in particular 0.1 to 95%, of an active substance of the formula I, 1 to 99% of a solid or liquid adjuvant and 0 to 25%, in particular 0.1 to 25%, of a surfactant.

In particular, preferred formulations have the following compositions: (%=percent by weight)

| Solutions | | |
|---|---|---|
| Active substance: | 5 to 95%, | preferably 10 to 80% |
| Solvent: | 95 to 5%, | preferably 90 to 20% |
| Surface-active agent: | 1 to 30%, | preferably 2 to 20%. |
| Emulsifiable concentrates | | |
| Active substance: | 10 to 50%, | preferably 10 to 40% |
| Surface-active agent: | 5 to 30%, | preferably 10 to 20% |
| Liquid carrier: | 20 to 95%, | preferably 40 to 80%. |
| Dusts | | |
| Active substance: | 0.5 to 10%, | preferably 2 to 8% |
| Solid carrier: | 99.5 to 90%, | preferably 98 to 92%. |
| Suspension concentrates | | |
| Active substance: | 5 to 75%, | preferably 10 to 50% |
| Water: | 94 to 25%, | preferably 90 to 30% |
| Surface-active agent: | 1 to 40%, | preferably 2 to 30%. |
| Wettable powders | | |
| Active substance: | 5 to 90%, | preferably 10 to 80% and particularly 20 to 60% |
| Surface-active agent: | 0.5 to 20%, | preferably 1 to 15% |
| Solid carrier: | 5 to 90%, | preferably 30 to 70%. |
| Granules | | |
| Active substance: | 0.5 to 30%, | preferably 3 to 15% |
| Solid carrier: | 99.5 to 70%, | preferably 97 to 85%. |

Whereas concentrated compositions are more likely to be preferred as commercial products, the final consumer generally uses dilute compositions. The applications can be diluted down to 0.001% of active substance.

The compositions can also contain further additives, such as stabilisers, anti-foaming agents, viscosity regulators, binders, tackifiers and fertilisers or other active substances for achieving special effects.

Agrochemical compositions of this type are a part of the present invention.

The examples which follow serve to illustrate the invention in greater detail, without limiting the latter. Temperatures are quoted in degrees centigrade.

PREPARATION EXAMPLES

Example 1

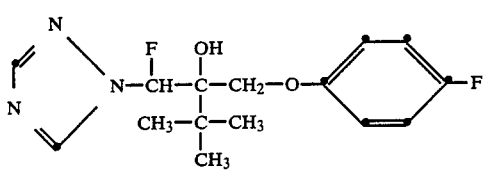

1-(4-Fluorophenoxy)-2-tert.-butyl-2-hydroxy-3-fluoro-3-(1H-1,2,4-triazol-1-yl)-propane (Compound 5.6)

(a) 1-Fluoro-1-(1H-1,2,4-triazol-1-yl)-3,3-dimethyl-2-butanone:

63.0 g of 1-bromo-1-fluoro-3,3-dimethyl-2-butanone are added slowly to a mixture of 23.0 g of 1,2,4-triazole and 44.2 g of potassium carbonate in 280 ml of ethyl methyl ketone. The reaction mixture is stirred for 18 hours at 45°–50° C. and is then filtered and evaporated. The residue is taken up in methylene chloride and washed with water. Drying and evaporating the organic phase gives 50.0 g of 1-fluoro-1-(1H-1,2,4-triazol-1-yl)-3,3-dimethyl-2-butanone, melting point 54°–55° C.

(b) 2-tert.-Butyl-2-[(1H-1,2,4-triazol-1-yl)-fluoromethyl]oxirane:

A mixture of 20 g of 1-fluoro-1-(1H-1,2,4-triazol-1-yl)-3,3-dimethyl-2-butanone, 13.5 g of potassium tertiary butylate, 24.0 g of trimethylsulfoxonium iodide, 80 ml of tetrahydrofuran and 20 ml of dimethyl sulfoxide is stirred at 60° C. for 6 hours. The reaction mixture is then taken up in ice water and extracted with ethyl acetate. The combined organic phases are washed with water and saturated sodium chloride solution, dried over sodium sulfate and evaporated. Crystallisation from petroleum ether gives 6.9 g of 2-tert.-butyl-2-[(1H-1,2,4-triazol-1-yl)-fluoromethyl]-oxirane, melting point 72°–74° C.

(c) 3.0 g of 2-tert.-butyl-2-[(1H-1,2,4-triazol-1-yl)fluoromethyl]-oxirane, 1.7 g of 4-fluorophenol and 0.3 g of potassium p-fluorophenate in 10 ml of diethylene glycol dimethyl ether are stirred at 140° C. for 5 hours. After cooling, the mixture is taken up in ice water and extracted with ethyl acetate. The combined organic phases are washed with water, saturated sodium chloride solution and 2N sodium hydroxide solution and again with saturated sodium chloride solution, dried over sodium sulfate and evaporated. Crystallisation from a 1:4 ether/hexane mixture gives 2.3 g of 1-(4-fluorophenoxy)-2-tert.-butyl-2-hydroxy-3-fluoro-3-(1H-1,2,4-triazol-1-yl)-propane, melting point 89°–90° C.

EXAMPLE 2

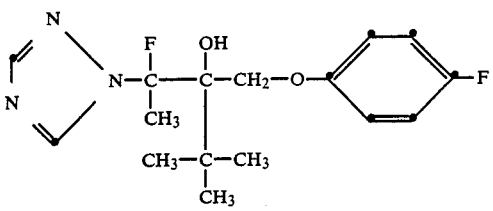

1-(4-Fluorophenoxy)-2-tert.-butyl-2-hydroxy-3-fluoro-3-methyl-3-(1H-1,2,4-triazol-1-yl)-propane (Compound 5.7).

(a) 2-Fluoro-2-(1H-1,2,4-triazol-1-yl)-4,4-dimethyl-3-pentanone:

20.0 g of 1-fluoro-1-(1H-1,2,4-triazol-1-yl)-3,3-dimethyl-2-butanone are added dropwise to a solution of 13.5 g of potassium tertiary butylate in 100 ml of tetrahydrofuran. After the mixture has been stirred for 0.5 hour, 15.6 g of methyl iodide are added dropwise and the mixture is stirred for 18 hours at 60° C. After cooling, the reaction mixture is taken up in ice water and extracted with ethyl acetate. The combined organic phases are washed with water and saturated sodium chloride solution, dried over sodium sulfate and evaporated. Distillation of the oily residue gives 14.0 g of 2-fluoro-2-(1H-1,2,4-triazol-1-yl)-4,4-dimethyl-3-pentanone, boiling point 48°–50° C./0.013 mbar.

(b) 2-tert.-Butyl-2-[1-fluoro-1-(1H-1,2,4-triazol-1-yl)ethyl]-oxirane:

12.0 g of 2-fluoro-2-(1H-1,2,4-triazol-1-yl)-4,4-dimethyl-3-pentanone are added dropwise to a mixture of 13.2 g of trimethylsulfoxonium iodide, 7.3 g of potassium tertiary butylate, 20 ml of dimethyl sulfoxide and 80 ml of tetrahydrofuran, and the reaction mixture is stirred for 18 hours at 80° C. After cooling, the mixture is taken up in ice water and extracted with ethyl acetate. The combined organic phases are washed with water and saturated sodium chloride solution, dried over sodium sulfate and evaporated. Distillation of the oily residue gives 6 g 2-tert.-butyl-2-[1-fluoro-1-(1H-1,2,4-triazol-1-yl)-ethyl]-oxirane, boiling point 60°–61° C./0.013 mbar.

(c) 6.0 g of 2-tert.-butyl-2-[1-fluoro-1-(1H-1,2,4-triazol-1-yl)-ethyl]-oxirane, 3.1 g of 4-fluorophenol and 0.4 g of potassium p-fluorophenate in 20 ml of diethylene glycol dimethyl ether are heated at 140° C. for 6 hours. After cooling, the reaction mixture is taken up in ice water and extracted with ethyl acetate. The combined organic phases are washed successively with water, saturated sodium chloride solution, 2N sodium hydroxide solution, water and saturated sodium chloride solution, dried over sodium sulfate and evaporated. Chromatography over silica gel using a 4:1 hexane/ethyl acetate mixture gives 1.6 g of 1-(4-fluorophenoxy)-2-tert.-butyl-2-hydroxy-3-fluoro-3-methyl-3-(1H-1,2,4-triazol-1-yl)-propane as a mixture of diastereomers, melting point 90°–93° C.

The compounds listed in the following tables are prepared analogously.

TABLE 1

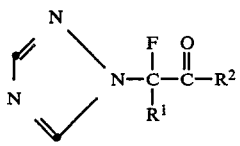

| No. | R¹ | R² | Physical data |
|---|---|---|---|
| 1.1 | H | $C_4H_9$—t | m.p. 54–55° C. |
| 1.2 | H | $C_3H_7$—i | |
| 1.3 | $CH_3$ | $C_4H_9$—t | b.p. 48–50° C./0.013 mbar |
| 1.4 | $CH_3$ | $C_3H_7$—i | |
| 1.5 | H | 4-Cl—$C_6H_4$—$CH_2$— | |
| 1.6 | H | 4-F—$C_6H_4$—$CH_2$— | |

TABLE 2

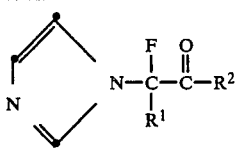

| No. | R¹ | R² | Physical data |
|---|---|---|---|
| 2.1 | H | $C_4H_9$—t | |
| 2.2 | H | $C_3H_7$—i | |
| 2.3 | $CH_3$ | $C_4H_9$—t | |
| 2.4 | $CH_3$ | $C_3H_7$—i | |
| 2.5 | H | 4-Cl—$C_6H_4$—$CH_2$— | |
| 2.6 | $CH_3$ | 4-Cl—$C_6H_4$—$CH_2$— | |

TABLE 3

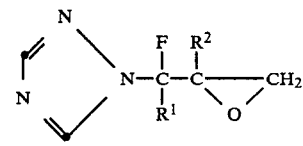

| No. | R¹ | R² | Physical data |
|---|---|---|---|
| 3.1 | H | $C_4H_9$—t | m.p. 72–74° C. |
| 3.2 | H | $C_3H_7$—i | |
| 3.3 | $CH_3$ | $C_4H_9$—t | b.p. 60–61° C./0.013 mbar |
| 3.4 | $CH_3$ | $C_3H_7$—i | |
| 3.5 | H | 4-Cl—$C_6H_4$—$CH_2$— | |
| 3.6 | H | 4-F—$C_6H_4$—$CH_2$— | |
| 3.7 | $C_2H_5$ | $C_4H_9$—t | |
| 3.8 | $C_6H_5$—$CH_2$— | $C_4H_9$—t | |
| 3.9 | 4-Cl—$C_6H_4$—$CH_2$— | $C_4H_9$—t | |
| 3.10 | 4-F—$C_6H_4$—$CH_2$ | $C_4H_9$—t | |
| 3.11 | $C_3H_7$—n | $C_4H_9$—t | |

TABLE 4

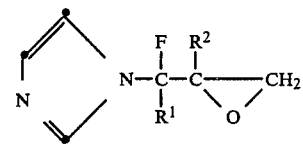

| No. | R¹ | R² | Physical data |
|---|---|---|---|
| 4.1 | H | $C_4H_9$—t | |
| 4.2 | H | $C_3H_7$—i | |
| 4.3 | $CH_3$ | $C_4H_9$—t | |
| 4.4 | $CH_3$ | $C_3H_7$—i | |
| 4.5 | H | 4-Cl—$C_4H_6$—$CH_2$— | |
| 4.6 | $CH_3$ | 4-Cl—$C_4H_6$—$CH_2$— | |
| 4.7 | $C_2H_5$ | $C_4H_9$—t | |

TABLE 5

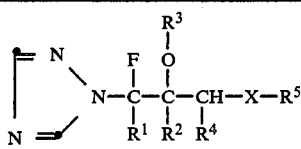

| No. | R¹ | R² | R³ | R⁴ | R⁵ | X | Physical data |
|---|---|---|---|---|---|---|---|
| 5.1 | H | $C_4H_9$—t | H | H | 4-Cl—$C_6H_4$— | O | m.p. 100–101° C. |
| 5.2 | $CH_3$ | $C_4H_9$—t | H | H | 4-Cl—$C_6H_4$— | O | m.p. 98–99° C. |
| 5.3 | $C_2H_5$ | $C_4H_9$—t | H | H | 4-Cl—$C_6H_4$— | O | |
| 5.4 | 4-Cl—$C_6H_4$—$CH_2$— | $C_4H_9$—t | H | H | 4-Cl—$C_6H_4$— | O | |
| 5.5 | 4-F—$C_6H_4$—$CH_2$— | $C_4H_9$—t | H | H | 4-Cl—$C_6H_4$— | O | |
| 5.6 | H | $C_4H_9$—t | H | H | 4-F—$C_6H_4$— | O | m.p. 89–90° C. |
| 5.7 | $CH_3$ | $C_4H_9$—t | H | H | 4-F—$C_6H_4$— | O | m.p. 90–93° C. |
| 5.8 | $C_2H_5$ | $C_4H_9$—t | H | H | 4-F—$C_6H_4$— | O | |
| 5.9 | 4-Cl—$C_6H_4$—$CH_2$— | $C_4H_9$—t | H | H | 4-F—$C_6H_4$— | O | |
| 5.10 | 4-F—$C_6H_4$—$CH_2$— | $C_4H_9$—t | H | H | 4-F—$C_6H_4$— | O | |
| 5.11 | H | $C_4H_9$—t | $CH_3$ | H | 4-F—$C_6H_4$— | O | |
| 5.12 | H | $C_4H_9$—t | $C_6H_5$—$CH_2$— | H | 4-F—$C_6H_4$— | O | |
| 5.13 | H | $C_4H_9$—t | H | H | 4-Br—$C_6H_4$— | O | m.p. 108–109° C. |
| 5.14 | H | $C_4H_9$—t | H | H | 4-$CH_3$—$C_6H_4$— | O | m.p. 96–98° C. |
| 5.15 | H | $C_4H_9$—t | H | H | $C_6H_5$ | O | |
| 5.16 | H | $C_4H_9$—t | H | H | 2-Cl—3-Cl—$C_6H_3$— | O | m.p. 127–128° C. |
| 5.17 | H | $C_4H_9$—t | H | H | 4-F—$C_6H_4$— | S | |
| 5.18 | $CH_3$ | $C_4H_9$—t | H | H | 4-Br—$C_6H_4$— | O | |
| 5.19 | $C_2H_5$ | $C_4H_9$—t | H | H | 4-Br—$C_6H_4$— | O | |
| 5.20 | $CH_3$ | $C_4H_9$—t | H | H | 4-$CH_3$—$C_6H_4$— | O | m.p. 136–137° C. |
| 5.21 | $CH_3$ | $C_4H_9$—t | H | H | $C_6H_5$ | O | |
| 5.22 | $CH_3$ | $C_4H_9$—t | $CH_3$ | H | 4-F—$C_6H_4$— | O | |
| 5.23 | $CH_3$ | $C_4H_9$—t | $CH_3$ | H | 4-Cl—$C_6H_4$— | O | |
| 5.24 | $CH_3$ | $C_4H_9$—t | $C_6H_5$—$CH_2$— | H | 4-F—$C_6H_4$— | O | |

TABLE 5-continued

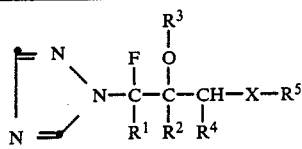

| No. | R¹ | R² | R³ | R⁴ | R⁵ | X | Physical data |
|---|---|---|---|---|---|---|---|
| 5.25 | $CH_3$ | $C_4H_9$—t | 4-Cl—$C_6H_4$—$CH_2$— | H | 4-F—$C_6H_4$— | O | |
| 5.26 | $CH_3$ | $C_4H_9$—t | $C_6H_5$—$CH_2$ | H | 4-Cl—$C_6H_4$— | O | |
| 5.27 | $CH_3$ | $C_4H_9$—t | 4-Cl—$C_6H_4$—$CH_2$— | H | 4-F—$C_6H_4$— | O | |
| 5.28 | $C_2H_5$ | $C_4H_9$—t | $CH_3$ | H | 4-F—$C_6H_4$— | O | |
| 5.29 | $CH_3$ | $C_4H_9$—t | —$COCH_3$ | H | 4-F—$C_6H_4$— | O | |
| 5.30 | $CH_3$ | $C_4H_9$—t | —$COCH_3$ | H | 4-Cl—$C_6H_4$— | O | |
| 5.31 | H | $C_4H_9$—t | H | H | 2-Cl—$C_6H_4$— | O | m.p. 121–122° C. |
| 5.32 | H | $C_4H_9$—t | H | H | 2-Cl—Cl—$C_6H_5$— | O | m.p. 163–165° C. |
| 5.33 | H | $C_4H_9$—t | H | H | 2-Cl—3-Cl—$C_6H_5$— | O | m.p. 135–136° C. |
| 5.34 | H | $C_4H_9$—t | H | H | $C_4H_9$—n | S | m.p. 150–160° C./0.06 mb |
| 5.35 | $CH_3$ | $C_4H_9$—t | H | H | 2-$CH_3$—3-$CH_3$—$C_6H_3$— | O | m.p. 147–148° C. |
| 5.36 | $CH_3$ | $C_4H_9$—t | H | H | 2-Cl—$C_6H_4$— | O | m.p. 158–159° C. |
| 5.37 | $CH_3$ | $C_4H_9$—t | H | H | $C_4H_9$—n | S | m.p. 125° C./0.01 mb |

TABLE 6

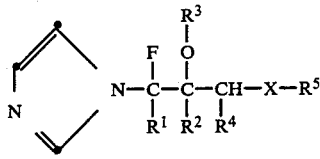

| No. | R¹ | R² | R³ | R⁴ | R⁵ | X | Physical data |
|---|---|---|---|---|---|---|---|
| 6.1 | H | $C_4H_9$—t | H | H | 4-Cl—$C_6H_4$— | O | |
| 6.2 | H | $C_4H_9$—t | H | H | 4-F—$C_6H_4$— | O | |
| 6.3 | H | $C_4H_9$—t | H | H | 4-$CH_3$—$C_6H_4$— | O | |
| 6.4 | H | $C_4H_9$—t | H | H | 4-Br—$C_6H_4$— | O | |
| 6.5 | H | $C_4H_9$—t | H | H | 4-$OCF_3$—$C_6H_4$— | O | |
| 6.6 | H | $C_4H_9$—t | H | H | 2-Cl—4-Cl—$C_6H_4$— | O | |
| 6.7 | $CH_3$ | $C_4H_9$—t | H | H | 4-Cl—$C_6H_4$— | O | |
| 6.8 | $CH_3$ | $C_4H_9$—t | H | H | 4-F—$C_6H_4$— | O | |
| 6.9 | $C_2H_5$ | $C_4H_9$—t | H | H | 4-F—$C_6H_4$— | O | |

FORMULATION EXAMPLES

Example 3

Examples of formulations of liquid active substances of the formula I (% = percent by weight)

| (a) Emulsion concentrates | (a) | (b) | (c) |
|---|---|---|---|
| Active substance | 20% | 40% | 50% |
| Ca dodecylbenzenesulfonate | 5% | 8% | 5.8% |
| Castor oil polyethylene glycol ether (36 moles of EO) | 5% | — | — |
| Tributylphenol polyethylene glycol ether (30 moles of EO) | — | 12% | 4.2% |
| Cyclohexanone | — | 15% | 20% |
| Mixed xylenes | 70% | 25% | 20% |

Emulsions of any desired concentration can be prepared from such concentrates by dilution with water.

| (b) Solutions | (a) | (b) | (c) | (d) |
|---|---|---|---|---|
| Active substance | 80% | 10% | 5% | 95% |
| Ethylene glycol monomethyl ether | 20% | — | — | — |
| Polyethylene glycol MW 400 | — | 70% | — | — |
| N—Methyl-2-pyrrolidone | — | 20% | — | — |
| Epoxidised coconut oil | — | — | 1% | 5% |
| Petroleum ether (boiling range 160–190° C.) | — | — | 94% | — |

The solutions are suitable for application in the form of very fine drops.

| (c) Granules | (a) | (b) |
|---|---|---|
| Active substance | 5% | 10% |
| Kaolin | 94% | — |
| Highly disperse silica | 1% | — |
| Attapulgite | — | 90% |

The active substance is dissolved in methylene chloride, the solution is sprayed onto the carrier and the solvent is then removed by evaporation in vacuo.

| (d) Dusts | (a) | (b) |
|---|---|---|
| Active substance | 2% | 5% |
| Highly disperse silica | 1% | 5% |
| Talc | 97% | — |
| Kaolin | — | 90% |

Ready-to-use dusts are obtained by mixing the carriers intimately with the active substance.

Example 4

Examples of formulations of solid active substances of the formula I (% = percent by weight)

| (a) Wettable powders | (a) | (b) |
|---|---|---|
| Active substance | 20% | 60% |
| Na ligninsulfonate | 5% | 5% |
| Na laurylsulfate | 3% | — |
| Na diisobutylnaphthalene-sulfonate | — | 6% |
| Octylphenol polyethylene glycol ether (7–8 moles of EO) | — | 2% |
| Highly disperse silica | 5% | 27% |
| Kaolin | 67% | — |

The active substance is thoroughly mixed with the adjuvants, and the mixture is thoroughly ground in a suitable mill. This gives wettable powders which can be diluted with water to give suspensions of any desired concentration.

| (b) Emulsion concentrate | |
|---|---|
| Active substance | 10% |
| Octylphenol polyethylene glycol ether (4-5 moles of EO) | 3% |
| Ca dodecylbenzenesulfonate | 3% |
| Castor oil polyglycol ether (36 moles of EO) | 4% |
| Cyclohexanone | 30% |
| Mixed xylenes | 50% |

Emulsions of any desired concentration can be prepared from this concentrate by dilution with water.

| (c) Dusts | (a) | (b) |
|---|---|---|
| Active substance | 5% | 8% |
| Talc | 95% | — |
| Kaolin | — | 92% |

Ready-to-use dusts are obtained by mixing the active substance with the carrier and grinding the mixture on a suitable mill.

| (d) Extruder granules | |
|---|---|
| Active substance | 10% |
| Na ligninsulfonate | 2% |
| Carboxymethylcellulose | 1% |
| Kaolin | 87% |

The active substance is mixed with the adjuvants, and the mixture is ground and moistened with water. This mixture is extruded and then dried in a stream of air.

| (e) Coated granules | |
|---|---|
| Active substance | 3% |
| Polyethylene glycol (MW 200) | 3% |
| Kaolin | 94% |

The active substance is finely ground and applied uniformly, in a mixer, to the kaolin, which has been moistened with polyethylene glycol. Dust-free coated granules are obtained in this way.

| (f) Suspension concentrate | |
|---|---|
| Active substance | 40% |
| Ethylene glycol | 10% |
| Nonylphenol polyethylene glycol ether (15 moles of EO) | 6% |
| Na ligninsulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The active substance is finely ground and intimately mixed with the adjuvants. This gives a suspension concentrate from which suspensions of any desired concentration can be prepared by dilution with water.

BIOLOGICAL EXAMPLES

Example 5

Action against *Puccinia graminis* on wheat (a) Residual protective action 6 days after being sown, wheat plants are sprayed with a spray liquor (0.06% of active substance) prepared from a wettable powder of the active substance. After 24 hours, the treated plants are infested with a uredospore suspension of the fungus. After being incubated for 48 hours at 95-100% relative humidity and approx. 20° C., the infested plants are placed in a greenhouse at approx. 22° C. Development of rust pustules is assessed 12 days after infestation.

(b) Systemic action 5 days after being sown, wheat plants are watered with a spray liquor (0.006% of active substance, based on the volume of soil) prepared from a wettable powder of the active substance. After 48 hours, the treated plants are infested with a uredospore suspension of the fungus. After being incubated for 48 hours at 95-100% relative humidity and approx. 20° C., the infested plants are placed in a greenhouse at approx. 22° C. Development of rust pustules is assessed 12 days after infestation.

Compounds from Table 1 have a good action against Puccinia fungi. Untreated, but infested, control plants show a 100% attack by Puccinia. Inter alia, compounds 5.6 and 5.7 inhibit attack by Puccinia to 0 to 5%.

Example 6

Action against *Cercospora arachidicola* on groundnut plants (a) Residual protective action Groundnut plants 10-15 cm high are sprayed with a spray liquor (0.02% of active substance) prepared from a wettable powder of the active substance, and are infested, 48 hours later, with a conidia suspension of the fungus. The infested plants are incubated for 72 hours at approx. 21° C. and a high humidity and are then placed in a greenhouse until the appearance of the typical leaf spots. The fungicidal action is assessed 12 days after infestation, on the basis of the number and size of spots which have appeared.

(b) Systemic action

Groundnut plants 10-15 cm high are watered with a spray liquor (0.06% of active substance, based on the volume of soil) prepared from a wettable powder of the active substance. After 48 hours, the treated plants are infested with a conidia suspension of the fungus and are incubated for 72 hours at approx. 21° C. and a high humidity. The plants are then placed in a greenhouse, and the fungal attack is assessed after 11 days.

In comparison with untreated, but infested, control plants (number and size of spots=100%), groundnut plants treated with active substances from Table 1 show a greatly reduced attack by Cercospora. This compounds 5.6 and 5.7 prevent the appearance of spots almost completely (0-10%) in the above tests.

Example 7

Action against *Erysiphe graminis* on barley (a) Residual protective action

Barley plants approx. 8 cm high are sprayed with a spray liquor (0.02% of active substance) prepared from a wettable powder of the active substance. After 3-4 hours, the treated plants are dusted with conidia of the fungus. The infested barley plants are placed in a greenhouse at approx. 22° C., and the fungal attack is assessed after 10 days.

(b) Systemic action

Barley plants approx. 8 cm high are watered with a spray liquor (0.006% of active substance, based on the volume of soil) prepared from a wettable powder of the active substance. In doing so, care is taken that the spray liquor does not come into contact with the parts of the plants above ground. After 48 hours, the treated plants are dusted with conidia of the fungus. The infested barley plants are placed in a greenhouse at approx. 22° C., and the fungal attack is assessed after 10 days.

Compounds of the formula I have a good action against Erysiphe fungi. Untreated, but infested, control plants show a 100% attack by Erysiphe. Amongst other compounds from Table 1, compound Nos. 5.6 and 5.7 inhibit fungal attack on barley to 0 to 5%.

Example 8

Residual protective action against *Venturia inaequalis* on apple shoots

Apple cuttings having fresh shoots 10-20 cm long are sprayed with a spray liquor (0.06% of active substance) prepared from a wettable powder of the active substance. After 24 hours, the treated plants are infested with a conidia suspension of the fungus. The plants are then incubated for 5 days at 90-100% relative humidity and are kept for a further 10 days in a greenhouse at 20°-24° C. The scab attack is assessed 15 days after infestation. Compounds 5.6, 5.7 and others inhibit the attack of the disease to less than 10%. Untreated, but infested, shoots show 100% attack by Venturia.

Example 9

Action against Botrytis cinerea on beans Residual protective action

Bean plants approx. 10 cm high are sprayed with a spray liquor (0.02% of active substance) prepared from a wettable powder of the active substance. After 48 hours, the treated plants are infested with a conidia suspension of the fungus. The fungal attack is assessed after the infested plants have been incubated for 3 days at 95-100% relative humidity and 21° C. In many cases the compounds from Table 1 inhibit the fungal infestation very greatly. For example, compounds Nos. 5.5, 5.7 and 5.14 prove fully effective (0 to 5% attack by the disease) at a concentration of 0.02%. The attack by Botrytis on untreated, but infested, bean plants was 100%.

Example 10

Inhibition of growth in cereals

The cereal species Hordeum vulgare (spring barley) and Secale (spring rye) are sown in plastic pots containing sterilised soil in a greenhouse and are watered as required. The shoots are sprayed with an aqueous spray liquor of an active substance of the formula I approx. 21 days after sowing. The quantity of active substance is equivalent to 0.3, 1 or 3 kg of active substance per hectare. The growth of the cereal is assessed 21 days after the application. This makes it possible to establish that cereal plants treated with active substances of the formula I show a considerable reduction in growth in comparison with untreated control plants.

Test results

The growth in height of the cereal plants as a percentage of the growth in height of the untreated control plants.

| Compound No. | 3 kg of AS/ha | | 1 kg of AS/ha | | 0.3 kg of AS/ha | |
|---|---|---|---|---|---|---|
| | Rye | Barley | Rye | Barley | Rye | Barley |
| 5.1 | 28 | 44 | 36 | 53 | 50 | 67 |
| 5.6 | 5 | 6 | 23 | 21 | 38 | 53 |
| 5.7 | 12 | 19 | 18 | 37 | 46 | 65 |
| 5.14 | 43 | 67 | 57 | 84 | 80 | 86 |
| 5.20 | 28 | 67 | 38 | 86 | 58 | 88 |

Example 11

Inhibition of growth in grasses

A grass mixture containing *Poa pratensis, Dactylis glomerata, Lolium perenne, Festuca rubra, Festuca ovina, Cynosurus crystatus, Agropyron repens* and *Bromus inermis* is sown in plastic trays containing a 6:3:1 soil/peat/sand mixture in a greenhouse, and the trays are watered as rerequired. The emergent grasses are cut back every week to a height of approx. 4 cm and, approx. 50 days after sowing and one day after the last cutting, are sprayed with an aqueous spray liquor of an active substance of the formula I. The quantity of active substance is equivalent to 0.3, 1, or 3 kg of active substance per hectare. The average growth of the grasses is assessed 21 days after the application, and it is found that the active substances according to the invention from Tables 5 and 6 effect a noticeable inhibition of growth.

Test results

The growth in height of the grasses as a percentage of the growth in height of the untreated control plants.

| Compound No. | 3 kg of AS/ha | 1 kg of AS/ha | 0.3 kg of AS/ha |
|---|---|---|---|
| 5.1 | 39 | 39 | 61 |
| 5.6 | 31 | 33 | 39 |
| 5.7 | 32 | 36 | 50 |
| 5.14 | 76 | 83 | 86 |
| 5.20 | 64 | 79 | 89 |

Example 12

Increasing the yield of soya beans

Soya beans of the "Hark" variety are sown in plastic vessels containing a 6:3:1 soil/peat/sand mixture, and are put into an airconditioned chamber. As the result of an optimum choice of temperature, illumination, addition of fertiliser and watering, the plants develop to the 5-leaf to 6-leaf trefoil stage after approx. 5 weeks. At this point the plants are sprayed with an aqueous liquor of an active substance of the formula I until they are thoroughly wetted. The concentration of active substance is equivalent to up to 3 kg of active substance per hectare. Evaluation is carried out out approx. 5 weeks after the application of the active substance. The active substances, according to the invention, of the formula I cause a noticeable increase in the number and weight of pods harvested, in comparison with untreated control plants.

Example 13

Inhibiting the vegetative growth of soya

Soya beans of the variety "Hark" are sown in plastic pots containing a 6:3:1 soil/peat/sand mixture, and are placed in a greenhouse and watered as required. 15 days after sowing, the plants are sprayed with an aqueous spray liquor of an active substance of the formula I until they are wetted. The combination of active substances is equivalent to 0.1, 0.5 and 1.5 kg of active substance per hectare. The growth of the plants is assessed 14 days after the application, and it is found that the active substances, according to the invention, from Tables 5 and 6 produce a noticeable inhibition of growth.

Test results

The growth in height of the soya plants as a percentage of the growth in height of the untreated control plants.

| Compound No. | 1.5 kg of AS/ha | 0.5 kg of AS/ha | 0.1 kg of AS/ha |
|---|---|---|---|
| 5.1 | 11 | 11 | 11 |
| 5.6 | 5 | 5 | 11 |
| 5.7 | 5 | 5 | 11 |
| 5.14 | 19 | 19 | 48 |
| 5.20 | 16 | 16 | 16 |

Example 14

Inhibition of growth in soil-covering plants (cover crops)

Test plants of the varieties Psophocarpus palustris and Centrosema pubescens are grown from cuttings in plastic trays containing a 1:1:1 soil/peat/sand mixture. After rooting, the small plants are transplanted into 9 cm pots and are watered as required. The plants are cultivated further in a greenhouse at a day temperature of 27° C. and a night temperature of 21° C., with an average duration of light of 14 hours (6,000 lux) and a humidity of 70%. The test plants are cut back to a height of approx. 15 cm and are sprayed with a spray liquor of the active substance (equivalent to 0.1, 0.3, 1 and 3 kg of active substance per hectare) 5 days after being cut back. 4 weeks after the application, the growth of the treated plants is compared with that of pruned, but untreated, control plants. This makes it possible to establish that compounds from Tables 5 and 6 initiate a marked inhibition of the growth of the soil-covering plants.

Test results

New growth of cover crop plants as a percentage of the green weight and growth in height of the new growth of the untreated control plants.

| Compound No. | kg of AS/ha | New growth of | | | |
|---|---|---|---|---|---|
| | | Centrosema pubescens | | Psophocarpus palustris | |
| | | green weight | growth in height | green weight | growth in height |
| 5.1 | 3 | 15 | 10 | 29 | 10 |
| | 1 | 26 | 10 | 35 | 10 |
| | 0.3 | 26 | 10 | 39 | 40 |
| | 0.1 | 59 | 30 | 59 | 30 |
| 5.6 | 3 | 15 | 10 | 26 | 10 |
| | 1 | 14 | 10 | 35 | 10 |
| | 0.3 | 30 | 10 | 23 | 10 |
| | 0.1 | 41 | 10 | 58 | 40 |
| 5.20 | 3 | 63 | 30 | 29 | 10 |
| | 1 | 59 | 40 | 58 | 40 |
| | 0.3 | 81 | 80 | 84 | 80 |
| | 0.1 | 85 | 80 | 97 | 100 |

Example 15

Terminating the growth of cotton

Cotton plants of the variety "Delta Pine" are sown in plastic vessels containing a 2:1 soil/peat mixture, and are cultivated in a greenhouse at temperatures of 20°–26° C. After 2 months the plants have developed to the 6-Leaf stage. At this point in time, the plants are sprayed with an aqueous dispersion of an active substance of the formula I until they are thoroughly wetted. The concentration of active substance is equivalent to 2.0 kg of active substance per hectare. Evaluation is carried out approx. 1 month after the application of the active substance. The active substances, according to the invention, of the formula I effect a noticeable reduction in new growth in comparison with untreated control plants.

What is claimed is:

1. 1-(4-Fluorophenoxy)-2-tert.-butyl-2-hydroxy-3-fluoro-3-(1H-1,2,4-triazol-1-yl)-propane.

2. 1-(4-Chlorophenoxy)-2-tert.-butyl-2-hydroxy-3-fluoro-3-(1H-1,2,4-triazol-1-yl)-propane.

* * * * *